(12) United States Patent
Kamb et al.

(10) Patent No.: US 6,623,922 B1
(45) Date of Patent: *Sep. 23, 2003

(54) METHODS FOR IDENTIFYING, CHARACTERIZING, AND EVOLVING CELL-TYPE SPECIFIC CIS REGULATORY ELEMENTS

(75) Inventors: Carl Alexander Kamb, Salt Lake City, UT (US); Giordano M. Caponigro, Salt Lake City, UT (US)

(73) Assignee: Deltagen Proteomics, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/800,664

(22) Filed: Feb. 14, 1997

(51) Int. Cl.$^7$ ............... C12Q 1/68; C12P 21/06
(52) U.S. Cl. ............... 435/6; 435/5; 435/69.1; 435/320.1; 435/DIG. 3; 435/DIG. 17; 435/DIG. 23; 435/DIG. 37; 536/23.1
(58) Field of Search ............... 435/6, 172.1, 172.3, 435/320.1, DIG. 3, DIG. 17, DIG. 23, DIG. 37, 69.1; 436/172; 536/23.1

(56) References Cited

U.S. PATENT DOCUMENTS

| | | | |
|---|---|---|---|
| 4,725,535 A | * 2/1988 | Sonenshine et al. | 435/6 |
| 5,217,889 A | 6/1993 | Roninson et al. | |
| 5,268,285 A | * 12/1993 | Rodgers et al. | 435/172.3 |
| 5,283,173 A | 2/1994 | Fields et al. | |
| 5,364,783 A | 11/1994 | Ruley et al. | |
| 5,401,629 A | 3/1995 | Harpold et al. | |
| 5,416,017 A | * 5/1995 | Burton et al. | |
| 5,466,785 A | * 11/1995 | De Framond | |
| 5,491,084 A | * 2/1996 | Chalfie | 435/1 |
| 5,569,588 A | 10/1996 | Ashby et al. | |
| 5,608,144 A | * 3/1997 | Baden et al. | |
| 5,691,137 A | 11/1997 | Rosbash et al. | |
| 5,824,469 A | * 10/1998 | Horowitz et al. | 435/6 |
| 5,928,888 A | 7/1999 | Whitney | |
| 5,945,276 A | 8/1999 | Wu et al. | |

FOREIGN PATENT DOCUMENTS

| | | |
|---|---|---|
| WO | WO 93/08701 | 5/1993 |
| WO | WO93/10245 | 5/1993 |
| WO | WO 95/16694 | 6/1995 |
| WO | WO 95/19988 | 7/1995 |
| WO | WO 97/20078 | 6/1997 |
| WO | WO 97/27212 | 7/1997 |
| WO | WO 97/48820 | 12/1997 |
| WO | WO 98/07886 | 2/1998 |

OTHER PUBLICATIONS

Horowitz et al Selection of new biological activities from random nucleotide sequences: evolutionary an practical considerations. Genome 31(30 112–117, 1985.*

Oliphant et al. The use of random–sequence oligonucleotides for determining concensus sequences. Methods in Enzymology 155: 568–582, 1987.*

Asoh et al, PNAS, vol. 91, pp 6982–6986, "Selection of DNA clones with enhancer sequences", 1994.*

Weinhert et al., The Journal of Immunology, vol. 154, pp4603–4612 "Cloning of the Murine CD5 Promoter and Its Tissue–Specific Regulation", 1995.*

Toyoda et al, Mammalian Genome, vol. 6, pp 426–428 "An enhanced promoter trap protocol", 1995.*

Kerr et al., Immunology, Supplement 2, pp 74–78 "In situ detection of transcriptionally active chromatin and genetic regulatory elements in individual viable mammalian cells", 1989.*

Anderson M.T., Tjioe I.M., Lorincz M.C., Parks D.R., Herzenberg L.A., Nolan G.P., Herzenberg, "Simultaneous Fluorescence–Activated Cell Sorter Analysis of Two Distinct Transcriptional Elements Within a Single Cell Using Engineered Green Fluorescent Proteins,", LA., *Proc. Natl. Acad. Sci.* (*USA*) 93: 16, 8508–8511 (1996).

Badia, E., Duchesne, M.J., Pons, M., and Nicolas, J.C., Membrane Targeting of Firefly Luciferase: A New Bioluminescent Reporter Gene, *Analytical Biochemistry* 217, 333–335 (1994).

Dorsky, David I., et al., "Detection of HIV–1 Infection with a Green Fluorescent Protein Reporter System", Journal of Acquired Immune Deficiency Syndromes and Human Retrovirology, Lippincott–Raven Publishers, Philadelphia, vol. 13, pp. 308–313 (1996).

Duchange N., Ochoa A., et al., Identification of an Enhancer Involved in the Melanoma–specific Expression of the Tumor Antigen Melanotransferrin Gene, *Nucleic Acids Res.* 20: 2853–2859 (1992).

Fuse N., Yasumoto K., et al., Identification of a Melanocyte–Type Promoter of the Microphthalmia–Associated Transcription Factor Gene, *Biochem. Biophys. Res. Commun.* 219: 702–707 (1996).

*Primary Examiner*—Padmashri Ponnaluri
(74) *Attorney, Agent, or Firm*—Fenwick & West LLP (57) ABSTRACT

The invention provides methods for efficient and rapid identification of cis-acting nucleic acid sequences that act in a cell-type specific manner to stimulate or repress the expression of linked genes or other neighboring sequences. The invention also provides methods for evolving novel regulatory sequences by in vitro manipulation of naturally occurring or synthetic cis acting nucleic acid sequences followed by screening and counterscreening steps. Furthermore, the invention provides methods for determining the mechanism by which cell-type specific cis regulatory sequences confer cell-type specific expression. Also provided are diagnostic methods based on the use of cell-type specific cis regulatory sequences.

12 Claims, 4 Drawing Sheets

OTHER PUBLICATIONS

Gervaix, Alain, et al., "A New Reporter Cell Line to Monitor HIV Infection and Drug Susceptibility in vitro", Proc. National Academy of Science, vol. 94, pp. 4653–4658 (Apr. 1997).

Hagen D.C., McCaffrey G., Sprague G.F. Jr., "Pheromone Response Elements Are Necessary and Sufficient for Basal and Pheromone–Induced Transcription of the FUS1 Gene of *Saccharomyces cerevisae,*" *Mol. Cell Biol.* 11: 6, 2952–61 (1991).

Herskowitz I., "Functional Inactivation of Genes by Dominant Negative Mutations," *Nature* 329: 219–222 (1987).

Kam–Leung, M., et al., "Examination of Mammalian Basic Helix–Loop–Helix Transcription Factors Using a Yeast One– Hybrid System," *DNA and Cell Biology,* 15:1, pp. 1–8, (1996).

Kavathes P., Sukhatme V.P., et al., Isolation of the Gene Encoding the Human T–lymphocyte Differentiation Antigen Leu–2 (T8) By Gene Transfer and Cdna Subtraction, *Proc. Natl. Acad. Sci.* (*USA*) 81: 7688–7692 (1984).

Koh J., Enders G.H., et al., "Tumour–Derived p16 Alleles Encoding Proteins Defective in Cell–Cycle Inhibition," *Nature* 375: 506–510 (1995).

Lewin B, *Genes V,* Chapter 29, Building the Transcription Complex: Promoters, Factors, and RNA Polymerases, Oxford University Press, Oxford, U.K. (1994), pp. 847–877.

Li, Joachim J., and Herskowitz, Ira, "Isolation of ORC6, a Component of the Yeast Origin Recognition Complex by a One–Hybrid System," *Science,* vol. 262, Dec. 17, 1993.

Luo Ying, et al., "Cloning and Analysis of DNA–Binding Proteins by Yeast One–Hybrid and One–Two–Hybrid Systems," *BioTechniques,* 20:4, pp. 564–568 (Apr. 1996).

Marcus, Sandra L., "Identification of COUP–TFII as a peroxisome proliferator response element binding factor using genetic selection in yeast: COUP–TFII activates transcription I yeast but anatagonizes PPAR signaling in Mammalian cells," *Molecular and Cellular Endocrinology* 120:31–39 (1996).

Qin Z., Kruger–Krasagakes S., et al., "Expression of Tumor Necrosis Factor by Different Tumor Cell Lines Results Either in Tumor Suppression or Augmented Metastasis," *Exp. Med.* 178: 355–360.

Serrano M., Hannon G.J., et al., "A New Regulatory Motif in Cell–Cycle Control Causing Specific Inhibition of Cyclin D/CDK4," *Nature* 366, 704–707 (1993).

Shibata K., Muraosa Y., et al., "Identification of a cis–Acting Element that Enhances the Pigment Cell–specific Expression of the Human Tyrosinase Gene," *J. Biol. Chem.* 267: 20584–20588 (1992).

Valdivia, Raphael H., and Falkow, Stanley, "Fluorescence–Based Isolation of Bacterial Genes Expressed Within Host Cells," *Science,* vol. 277, Sep. 26, 1997.

Wang, Michael J., et al., "Molecular cloning of the olfactory neuronal transcription factor Olf–1 by genetic selection in yeast," *Nature,* 364:121–126 (Jul. 8, 1993).

Yokoyama K., Yasumoto K., et al., "Cloning of the Human DOPAchrome Tautomerase/Tyrosinase–related Protein 2 Gene and Identification of Two Regulatory Regions Required for its Pigment Cell–specific Expression," *J. Biol. Chem.* 269: 27080–27087 (1994).

Zou, Yimin, Evans, Sylvia, Chen, Ju, Kuo, Hai–Chien, Harvey, Richard P., and Chien, Kenneth R., "CARP, a cardiac ankyrin repeat protein, is downstream in the Nkx2–5 homeobox gene pathway," *Development* 124, 793–804 (1997).

Cornwell, Richard D., et al., "Description of the leukocyte function–associated antigen 1 (LFA–1 or CD11a) promoter," Proceedings of the National Academy of Sciences of the United States of America, 90:4221–4225 (May 1993).

Baillie, Rebecca A., et al., "Transient transfection of chick–embryo hepatocytes," J Nutr. Bioechem 4:431–439 (Jul. 1993).

Valdivia, Raphael H. and Falkow, Stanley, "Bacterial Genetics By Flow Cytometry: Rapid Isolation Of *Salmonella typhimurium* Acid–inducible Promoters By Differential Fluorescence Induction," 1996 *Blackwell Science Ltd., Molecular Microbiology,* 22(2), pp. 367–378.

Alberts B., Bray D., et al. (Eds.), *Molecular Biology of the Cell,* Chapter 10, Control of Gene Expression, Second Edition, Garland Publishing, Inc., New York and London, (1989), pp. 551–599.

Bellen H.J., O'Kane C.J., et al., "P–element–mediated Enhancer Detection: A Versatile Method to Study Development in Drosophila," *Genes Dev.* 3: 1288–1300 (1989).

Chalfie M., Tu Y, et al., "Green Fluorescent Protein as a Marker for Gene Expression," *Science* Feb. 11; 263:802–805 (1994).

Cormack B.P., Valdivia R.H., and Falkow S., "FACS–Optimized Mutants of the Green Fluorescent Protein (GFP)," *Gene* 173: 33–38 (1996).

Fieck A., Wyborski D.L., and Short J.M., "Modifications of the *E.Coli* Lac Repressor for Expression in Eukaryotic cells: Effects of Nuclear Signal Sequences on Protein Activity and Nuclear Accumulation," *Nucleic Acids Res.* 20: 1785 (1992).

Hanahan D., "Heritable Formation of Pancreatic β–Cell Tumours in Transgenic Mice Expressing Recombinant Insulin/Simian Virus 40 Oncogenes," *Nature* May 11; 20: 2233–2239 (1985).

Harrison R.W., and Miller J.C., "Functional Identification of Genes Up– and Down–Regulated by Glucocorticoids in AtT–20 Pituitary Cells Using an Enhancer Trap," *Endocrinology* Jul; 137:2758–2765 (1996).

Koh J., Enders G.H., et al., "Tumour–Derived p16 Alleles Encoding Proteins Defective in Cell–Cycle Inhibition," *Nature* 375: 506–510 (1995).

Kozak M., "Point Mutations Define a Sequence Flanking the AUG Initiator Codon That Modulates Translation by Eukaryotic Ribosomes," *Cell* Jan. 31; 44: 283–292 (1986).

Iida A., Chen S.T., et al., "Inducible Gene Expression by Retrovirus–Mediated Transfer of a Modified Tetracycline––Regulated System," *J. Virol* 70: 6054–6059 (1996).

Myers RM, Tilly K, and Maniatis T., "Fine Structure Genetic Analysis of a β–Globin Promoter," *Science* 232: 613–618 (1986).

Ross J., "mRNA Stability in Mammalian Cells," *Microbiol. Rev.:* 423–450 (1995).

Simmons D., and Seed B. "Isolation of a cDNA Encoding CD33, a Differentiation Antigen of Myeloid Progenitor Cells," *J Immunol* 141: 2797–2800 (1988).

Wasylyk B., Wasylyk C., and Chambon P., "Short and Long Range Activation by the SV 40 Enhancer," *Nucleic Acids Res.* Jul. 25; 12: 5589–5608 (1984).

Wilkinson G.W., and Akrigg A., "Constitutive and Enhanced Expression from the CMB Major IE Promoter in a Defective Adenovirus Vector," *Nucleic Acids Res.* May 11; 20: 2233–2239 (1992).

* cited by examiner

METHODS FOR IDENTIFYING, CHARACTERIZING, AND EVOLVING CELL-TYPE SPECIFIC CIS REGULATORY ELEMENTS

FIELD OF THE INVENTION

The present invention comprises procedures for identifying, characterizing, and evolving cis-acting nucleic acid sequences that act in a cell-type specific manner to stimulate or repress the expression of linked genes or other neighboring sequences.

BACKGROUND OF THE INVENTION

A variety of cis-acting nucleic acid sequences influence expression levels of genes in prokaryotic and eukaryotic cells. These sequences act at the level of mRNA transcription, mRNA stability, or mRNA translation (Alberts B., Bray D., et al. (Eds.), *Molecular Biology of the Cell*, Second Edition, Garland Publishing, Inc., New York and London, (1989)). In the cases of RNA stability and translation, the cis sequences are present on the RNA molecules themselves. In the case of transcription, the cis sequences may be present either on the transcribed sequences or they may reside nearby in regions of the gene that are not transcribed.

In prokaryotes that have been studied, most of the transcriptional control sequences lie immediately upstream of the RNA start site in an area called the promoter. In the case of *E. coli* promoters, for example, the consensus promoter sequence consists of two regions, one located about 10 basepairs upstream of the start site, and one located about 35 bases upstream. These sequences coordinate the binding of RNA polymerase, the principal enzyme involved in transcription. Other sequences also influence the level of transcription of *E. coli* genes. These sequences include repressor-binding sites and other sites that bind ancillary factors that regulate interaction between RNA polymerase and the promoter.

In prokaryotes such as *E. coli*, little regulation is exerted at the level of transcript stability, probably because the cell division cycle is typically very short. Thus, transcript half-lives are generally only a few minutes. However, considerable control is exercised at the level of translation. In *E. coli*, sequences immediately upstream of the translational start site (Shine-Dalgarno sequences) mediate the binding of mRNA molecules to the ribosome, and hence, the efficacy of translation.

In eukaryotes, the control of gene expression is more complex but some of the same principles are involved. Gene expression levels are influenced not only by cis sequences that bind transcription regulatory factors, but also by sequences that affect the overall conformation of the DNA in the vicinity of the gene in question. These effects on chromatin structure are less well understood, but are likely to be very significant. It is thought that structural components such as histones and other proteins pack or unpack in a regulated fashion to affect the global and local conformations of DNA, and thus the accessibility of cis regulatory elements in or near genes.

The promoter regions of eukaryotic genes are also more complex than prokaryotic promoters and generally involve binding sites for numerous factors in addition to the RNA polymerase holoenzyme. Certain sequences are involved specifically in the process of transcription initiation, such as the TATA box (Myers R M, Tilly K, and Maniatis T., *Science* 232: 613–618 (1986)), whereas other sequences act to influence the rate of initiation. These latter sequences have been called enhancers, and they have the property of being relatively insensitive to position in the promoter (Wasylyk B., Wasylyk C., and Chambon P., *Nucleic Acids Res.* July 25; 12: 5589–5608 (1984)). Many enhancers are located several kilobasepairs away from the gene whose expression level they regulate.

Because cell generation times in eukaryotes are typically longer than in prokaryotes, transcript stability is an important mode of regulation. For instance, some transcripts such as c-Fos have half lives on the order of minutes, while others have half lives on the order of hours. Sequences located at a variety of sites within the transcript influence the susceptibility of specific mRNA molecules to degradation by RNases within the cell (Ross J., *Microbiol Rev.*: 423–450 (1995).

Translational regulation also plays a significant role in eukaryotic gene expression. Secondary structure in particular transcripts can influence translation rates, as can codon usages. In addition, the sequence composition surrounding the translational start site (the Kozak-consensus sequence) is an important factor in translational efficiency (Kozak M., *Cell* January 31; 44: 283–292 (1986)).

In both prokaryotes and eukaryotes, the activity of many promoters is regulated according to the state of the cell. In metazoans, the situation can be much more complex because certain promoters may be active only in specific cell lineages. Thus, their activity must be regulated according to the particular time in development of the organism and the specific cell type.

Genetic screens and selections allow identification of regulatory elements in genes. If a powerful genetic selection or screen is enforced on a population of cells, it is possible to identify variants that have properties worthy of further study. Multiple rounds of selection or screening may permit the ultimate identification of variants in cases where a single round of selection/screen is not sufficient to enrich the population of desired variants. Genetic selections typically involve conditions whereby wild type cells die or grow slowly compared to variant cells in the population. Such conditions may be forced upon a culture of cells or a population of organisms. An equivalent process may involve a "screen and pluck" approach, where interesting variants are identified from the population, separated, and allowed to replicate in isolation. Such a process ultimately leads to an enrichment in the selected population for variants with the desired phenotypic traits, and a diminution of cells or organisms with the parental phenotype.

Numerous approaches have been applied to the identification and study of cis regulatory sequences. However, in general the approaches have been relatively labor intensive and slow. In addition, the approaches have generally been aimed at the study of the behavior of cis sequences in the natural setting; i.e., the intention has been to study the normal regulation of such sequences in the cell.

In certain cases, cis sequences have been deliberately engineered to control expression of particular genes in desirable ways. For example, it is useful to regulate tissue specificity and levels of exogenous genes using defined regulatory elements. This may involve fine control over tissue specificity, e.g., as in expression of the SV40 T antigen (TAg) in pancreatic islet beta cells by linking the TAg gene to the insulin promoter (Hanahan D., *Nature* May 11; 20: 2233–2239 (1985)), or it may involve efforts to maximize expression, e.g., as in the use of viral regulatory sequences such as the CMV enhancer (Wilkinson G. W., and Akrigg A., *Nucleic Acids Res*. May 11; 20: 2233–2239 (1992)), or it may involve efforts to modulate expression levels from low to high, e.g., as in the LacSwitch (Fieck A., Wyborski D. L., and Short J. M., *Nucleic Acids Res*. 20: 1785 (1992)) and TetSwitch systems (Iida A., Chen S. T., et al., *J. Virol* 70: 6054–6059(1996)).

A variety of techniques have been used in to identify cis sequences that regulate gene expression. These include biochemical methods that identify sites of interaction with protein factors, comparative sequence analysis, characterization of regulatory mutations in genes, and assay of deliberately constructed sequence variants for their effects on gene expression (Latchman David S., *Eukaryotic Transcription Factors* Second Edition, Academic Press, London (1996); McKnight S. L., and Yamamoto K. R. (Eds.), *Transcriptional Regulation*, CHSL Press, New York (1992)). Such methods have the drawback that they often require some a priori knowledge of the nucleic acid sequence of the regions of interest. In addition, several methods have been employed to "trap" cis sequences that have promoter activity. In prokaryotes, this often involves insertion of reporter constructs (involving, e.g., the LacZ gene) into the vicinity of genes such that the reporter is brought under the control of specific promoters. Screening or selecting for expression of the reporter permits the identification of promoters that have particular properties; for example, promoters that are active only under conditions of stress in the cell (Kenyon C. J., and Walker G. C., *Proc. Natl. Acad. Sci. USA* May; 77: 2819–2823 (1980)). Similar methods have been applied in metazoans, particularly in *Drosophila melanogaster* to identify genes with interesting expression patterns, and hence, promoters/enhancers. Such methods often fall under the rubric of "enhancer trap" or "promoter trap" screens (Bellen H. J., O'Kane C. J., et al., *Genes Dev* 3: 1288–1300 (1989)). Such methods suffer from the limitations of being slow and labor intensive. In addition, they are generally intended to identify natural sequences that have specific regulatory properties in vivo, as opposed to artificial sequences with preselected behavior.

In mammalian cells, a variety of methods have been used to identify interesting regulatory sequences by genetic screens or selections. In the general approach used for identification of cis regulatory elements through genetics, reporter constructs or selectable markers are used. Reporter genes that have been used include the choline acetyl transferase (CAT) gene (Thiel G., Petersohn D., and Schoch S., *Gene* February 12; 168: 173–176 (1996)), the LacZ gene from *E. coli* (Shapiro S. K., Chou J., et al., *Gene* November; 25: 71–82 (1983)), the green fluorescent protein (GFP) gene from jellyfish (Chalfie M. and Prashner D. C., U.S. Pat. No. 5,491,084), and numerous others. Genes that function as selectable markers (i.e., conditions can be chosen such that cells lacking the marker die) can also be used. Such selectable markers include genes that encode resistance to hygromycin, mycophenolic acid, neomycin, and other agents (Ausubel F. M. Brent R. et al. (Eds.) *Current Protocols in Molecular Biology*, John Wiley and sons, New York (1996)).

In one type of enhancer trap screen used for identifying cis sequences from mammalian cells, retroviruses that include reporter genes are used to infect cells. Depending on the more-or-less random integration of the virus in particular cells, the reporter construct is placed in a position where it can respond to specific cis sequences present in the host cell chromosome. This approach is exemplified by Ruley H. E. and von Melchner H., U.S. Pat. No. 5,364,783. In other approaches, selection schemes can be designed which allow identification of cis sequences that respond in a defined manner; e.g., they mediate induction or suppression by glucocorticoids (Harrison R. W., and Miller J. C., *Endocrinology* July; 137:2758–2765 (1996)). Limitations of these methods include the inability to easily select for cis sequences that control gene expression in a cell-type dependent manner and the reliance of such methods on the capacity of a vector to integrate into the host cell genome.

Control of gene expression is an exceedingly important issue in the detection and treatment of human disease. Many diseases can be viewed as defects in proper regulation of gene expression. One of the clearest illustrations is cancer, a heterogeneous disease caused by accumulated mutations that result in loss of cellular growth control. A combination of inactivation of tumor suppresser genes, and activation of oncogenes produces the cancer cell phenotype. Thus, disease detection and prognosis may be facilitated by methods that permit the analysis of gene expression profiles in cells, and by strategies that take advantage of the tendency of specific cell types to express certain genes. Information relevant to such strategies for diagnosis may also be relevant to therapy. For example, sequences that ensure proper regulation of particular gene therapeutics are valuable in controlling side effects of the therapeutic agent.

A simple method is needed for identification and characterization of cis sequences that control gene expression in a cell-type dependent manner. This method should permit identification of sequences that allow specific expression; that is, high expression in one cell type, and low expression in another. The method should be general, i.e. it should be applicable to nearly all cell types; it should be rapid; and it should be useful for evolving cis sequences from natural or synthetic building blocks into sequences with characteristics that may differ from cis regulatory sequences found in nature. In addition, the method should allow the mechanism of this specific expression to be directly elucidated. Cis sequences with such defined properties would have tremendous potential value in the diagnosis and treatment of diseases.

In the case of diagnosis, cell-type specific cis sequences would offer the possibility of developing an assay based on gene expression for detection of particular diseased tissues or pathogens. For instance, a cis sequence linked to a reporter could be introduced into biopsy samples and the expression of the reporter could be monitored by a colorimetric assay or by the polymerase chain reaction (PCR) (Ausubel F., Brent R., et al., 1996). If a tumor-specific cis sequence were linked to the reporter, a positive result of the assay (i.e., expression of the reporter gene) would indicate the presence of malignant cells in the biopsy. Thus, cis sequences that regulate gene expression in a cell-specific manner open up novel opportunities for potentially very sensitive and general diagnostic testing.

In the case of therapy, it is often advantageous—even essential—to confine the expression of a transgene (a gene introduced into germline or somatic tissue) to a particular cell type. For example, if a cis sequence were found that conferred expression of linked genes only in tumor cells and not in normal cells, this sequence would be useful as a mechanism for directing selective expression of genes in tumor cells. Normal cells that inadvertently picked up the gene would not be affected because the gene would remain silent. Another example involves virus-infected cells. If a cis regulatory sequence were identified that was active only in infected cells, these cells could be targeted for elimination by an appropriate construct that included such a sequence.

Finally, if cell-type specific cis sequences were identified, they would be useful in creating reporter constructs that could detect and serve as a surrogate for the phenotypic state of a specific cell type.

SUMMARY OF THE INVENTION

The invention comprises a combination of tools that together allow cis sequences with cell-type specific effects on gene expression to be identified. The tools include a reporter gene, an appropriate expression vector, a genetic library, and a method for screening or selecting cells based on reporter expression level.

In a preferred embodiment, the expression vector is designed so that reporter expression is completely disabled or occurs at a low level unless appropriate cis sequences are located in the expression construct to activate transcription. Such cis sequences may be promoters, enhancers, or both. This "dead" expression vector may be used as a cloning vehicle for nucleic acid fragments derived from a variety of sources, such as genomic DNA, mRNA, cDNA, or from oligonucleotide synthesis. The fragments may range in size from a few base pairs up to several kilobasepairs, depending on the objective of the particular experiment. These fragments are inserted into the vector to generate a library of cloned fragments. The library is introduced into one type of host cell (e.g., a tumor cell) and after a period of time sufficient to allow expression of the reporter, the cells are screened to select cells that express the reporter. In a preferred embodiment, GFP or any molecule capable of being labeled directly or indirectly with a fluorophore is used as the reporter and selection may be accomplished using a flow sorter device such as a fluorescence-activated cell sorter (FACS) by measuring the fluorescence signal from the reporter and collecting positive ("bright") cells (Autofluorescent proteins; AFPs™ Quantum Biotechnologies, Inc.; Robinson P. J., Darzynkiewicz Z., et al. *Current Protocols in Cytometry*, Published in Affiliation with the International Society for Analytical Cytology (1997). These cells contain expression vectors harboring library fragments that have brought the previously dead construct to life; e.g., promoters active in the particular cell type used for the experiment. Present-day FACS machines easily can sort $10^7$ to $10^8$ cells per hour. Thus millions of sequences can be screened in a short period of time to identify positive or negative cells.

To recover cell-specific cis sequences, a counterscreening step is performed. In one embodiment of this step, the sub-library of fragments that activate transcription is moved from a first host cell into a second host cell (e.g. a non-tumor cell). In a preferred embodiment, the second host cell is passed through a FACS, but this time negative ("dim") cells are recovered. In some circumstances it may be helpful to include an independent reporter to ensure that the dim cells contain the expression construct. The sub-library of fragments contained in this fraction of cells is retrieved. The sub-library of fragments retrieved from the recovered second host cells may be moved back into the first host cells and the screening and counterscreening procedure can be repeated several times to ensure that fragments are recovered from the experiment which are selectively active in one cell type and not the other. These fragments can be characterized individually for activity and also by nucleic acid sequence analysis.

In another preferred embodiment, the process begins with a "live" expression vector and reverses the selection criteria so that first host cells that do not express the reporter are selected in the screening step and second host cells that do express the reporter are selected in the counterscreening step. This embodiment of the method can be used to identify cell-type specific sequences that act as repressors of gene expression. In addition, it is possible to evolve novel cell-type specific sequences by mutation in vitro, by recombination in vitro, or by other mechanisms.

Comparisons of the nucleic acid sequences of cell-type specific cis sequences identified according to the methods of the invention with existing databases may allow identification of known promoter elements. Finally, the sequences identified in accordance with the methods of the invention can be used in subsequent biochemical experiments to identify factors from the two host cell types that are responsible either for activation of expression, or for repression. For example, cell extracts of the two host cell types can be incubated with the fragment, and the bound factors can be characterized. It may be possible to use mass spectrometry to identify the masses of peptide fragments derived from bound proteins by comparison to the EST database (Shevchenko A., Jensen O. N., et al., *Proc. Natl. Acad. Sci. USA* December 10; 93:14440–14445 (1996)). Thus, an underlying mechanism for the behavior of the cis sequences can be readily determined.

BRIEF DESCRIPTION OF THE FIGURES

FIG. 2: Distribution of fluorescence intensities and selection of tails of distribution.

(A.) Curve labeled "population before sorting" illustrates fluorescence intensity profile of the first host cells containing the library shaded area under the right side of the curve illustrates the fraction of first host cells selected as the "bright" population. Curve labeled "bright population after sorting" illustrates the fluorescence intensity profile of the bright population re-run through the FACS.

(B.) Curve labeled "bright population after cycle" illustrates fluorescence intensity profile of second host cells containing sub-library of fragments isolated from the bright population. Shaded area under the left side of the curve illustrates the fraction of second host cells selected as the "dim" population. Curve labeled "dim population after sorting" illustrates the fluorescence intensity profile of the dim population re-run through the FACS.

(C.) Curve labeled "dim population after cycle" illustrates fluorescence intensity profile of first host cells containing sub-library of fragments isolated from the dim population FIG. 3: Flow chart of process. The input genetic library is symbolized by the collection of double helices [1] in the upper right of the drawing. The library is introduced into the first host cell type, illustrated by circles [2]. These first host cells are sorted or selected based on the level of reporter expression [3]. The selected first host cells [4] are collected while the rest of the first host cells are discarded [5]. A sub-library of inserts is prepared from the selected first host cells [6], and is introduced into the second host cell type, illustrated by diamonds [7]. The second host cells are sorted or selected based on the level of reporter expression [8]. The selected second host cells are collected [9], while the rest of the second host cells are discarded [10]. After a sufficient number of enrichment cycles, insert sequences can be isolated for nucleic acid sequence analysis [12].

DETAILED DESCRIPTION OF PREFERRED EMBODIMENTS

Definitions

The terms "genetic library" or "library" are interchangeably used to refer to a collection of nucleic acid fragments that may individually range in size from about a few base pairs to about a million base pairs. These fragments are contained as inserts in vectors capable of propagating in certain host cells such as bacterial, fungal, mammalian, insect, or plant cells.

The term "sub-library" refers to a portion of a genetic library comprising one or more nucleic acid fragments that has been isolated by application of a specific screening or selection procedure.

The term "vector" refers to a nucleic acid sequence that is capable of propagating in particular host cells and can accommodate inserts of foreign nucleic acid. Typically, vectors can be manipulated in vitro to insert foreign nucleic acids and the vectors can be introduced into host cells such that the inserted nucleic acid is transiently or stably present in the host cells.

The term "expression vector" refers to a vector designed to express inserted nucleic acid sequences. Such vectors may contain a powerful promoter located upstream of the insertion site.

The term "expression" in the context of nucleic acids refers to transcription and/or translation of nucleic acids into mRNA and protein products.

The term "collection of nucleic acid fragments" refers to a set of nucleic acid molecules from any source. For example, a collection of nucleic acid fragments may comprise total genomic DNA, genomic DNA from one or more chromosomes, cDNA that has been reverse-transcribed from total cellular RNA or from messenger RNA (mRNA), total cellular RNA, mRNA, or a set of nucleic acid molecules synthesized in vitro either individually, or using combinatorial methods.

The term "host cell" refers to a cell of prokaryotic or eukaryotic origin that can serve as a recipient for a vector that is introduced by any one of several procedures. The host cell often allows replication and segregation of the vector that resides within. In certain cases, however, replication and/or segregation are irrelevant; expression of vector or insert DNA is the objective. Typical bacterial host cells include *E. coli* and *B. subtilis*; fungal host cells include *S. cerevisiae* and *S. pombe*; insect host cells include those isolated from *D. melanogastor, A. aegypti,* and *S. frugiperda*; plant cells include those isolated from *A. thaliana,* and *Z maize*; and mammalian cells include those isolated from human tissues and cancers including melanocyte (melanoma), colon (carcinoma), prostate (carcinoma), and brain (glioma, neuroblastoma, astrocytoma).

The term "reporter gene" refers to nucleic acid sequences for which screens or selections can be devised. Reporter genes may encode proteins ("reporters") capable of emitting light such as GFP (Chalfie M., Tu Y, et al., *Science* February 11; 263 :802–805 (1994)), or luciferase (Gould S. J., and Subramani S., *Anal Biochem* November 15; 175: 5–13 (1988)), or genes that encode cell surface proteins detectable by antibodies such as CD20 (Koh J., Enders G. H., et al., *Nature* 375: 506–510 (1995)). Preferably, the reporters allow the activity of cis regulatory sequences to be monitored in a quantitative manner. Alternatively, reporter genes can confer antibiotic resistance such as hygromycin or neomycin resistance (Santerre R. F., et al. *Gene* 30: 147–156 (1984)).

The terms "cis regulatory sequence," "cis sequence," "regulatory sequence," or "regulatory element" are interchangeably used to refer to a nucleic acid sequence that affects the expression of itself or other sequences physically linked on the same nucleic acid molecule. Such sequences may alter gene expression by affecting such things as transcription, translation, or RNA stability. Examples of cis regulatory sequences include promoters, enhancers, or negative regulatory sequences (Alberts B., Bray D., et al., 1989).

The term "nucleic acid transfer" refers to the introduction of exogenous or foreign nucleic acid into a host cell. Methods that are well known in the art including transfection, transformation, electroporation, lipofection, microinjection, ballistic delivery, DEAE dextran, viral infection, and calcium phosphate coprecipitation (Ausubel F. M., Brent R., et al., 1996; Sambrook J. Fritsch E. F. and Maniatis T., *Molecular Cloning: A Laboratory Manual* Second Edition, CSHL Press, New York, (1989)).

Expression Vectors

Expression vectors are used to identify cell-type specific cis regulatory sequences according to the methods of the invention. In preferred embodiments for identifying enhancers or promoters, the vector is designed so that the expression of a reporter is controlled by a "dead," or nonfunctional, promoter. This promoter lacks at least one of the cis sequences necessary for efficient reporter expression. Thus, introduction of the reporter construct into cells generally results in low or absent expression of the reporter. However, if appropriate cis sequences from the library, e.g., enhancers, are inserted upstream of the reporter, high levels of expression ensue. Conversely, to identify negative regulatory sequences according to the methods of the invention, the vector is designed to express moderate to high levels of reporter in the absence of negative regulatory sequence inserts from the library.

There are numerous expression vectors known in the art that are readily available fore use in the present invention (Ausubel F. M., Brent R., et al., 1996; Sambrook J., Fritsch E. F., and Maniatis T., 1989). Some of these are tailored for use in specific cell types, but most are designed to be used in a wide variety of cell types. In mammalian cells, viral transcriptional regulatory elements are a typical choice for driving expression of exogenous genes. In the case of enhancer/promoter trapping methods of the invention, it is necessary to use vectors that lack cis sequences needed to drive reporter expression, and therefore are not functional unless these missing sequences are inserted nearby.

It is possible to choose or create a vector that contains the reporter gene with no known promoter/enhancer elements located upstream. If such vectors are used in the present invention, activation of the reporter gene requires that all necessary sequences be introduced during library construction. Alternatively, it is possible to use expression vectors whose promoters have been deliberately crippled by in vitro modification or in vivo screens or selections. For example, promoters that have undergone deletion of critical elements may be used according to the present invention to identify cis sequences that restore activity.

Figure 1:
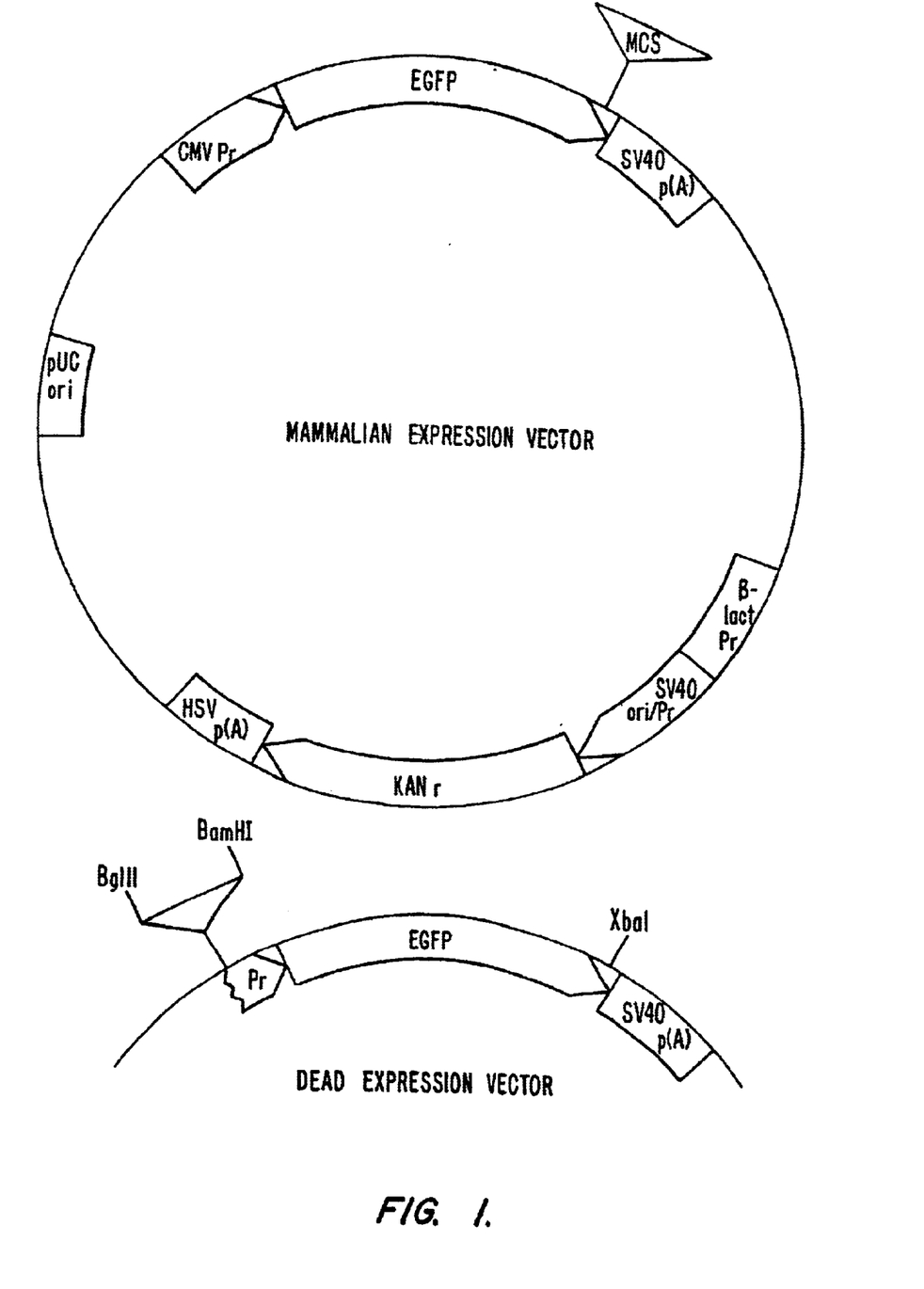
FIG. 1: Mammalian expression vector (FIG. 1*a*) and "dead" expression vector (FIG. 1*b*) diagrams. The mammalian expression vector is pEGFP-C1 (Clontech Laboratories, Palo Alto, Calif.; GenBank accession number U55763). MCSS is the multiple cloning site. The dead expression vector is derived from PEGFP-C1 and contains BglII and BamH1 sites inserted upstream of the TATA box of the truncated CMV promoter.

For the purposes of the present invention, an expression vector that contains a reporter gene flanked downstream by a poly(A) addition sequence, e.g., derived from the SV40 TAg gene, may be used. This type of expression vector is illustrated in FIG. 1. The reporter may be flanked upstream of its initiation codon by a TATA box, capable of binding RNA polymerase II (Pol II), and then by a cloning site. Alternatively, the vector may lack the Pol II binding site entirely. The cloning site, typically located upstream of the reporter, is used to introduce DNA fragments to produce a library in the expression vector. This library is used in subsequent screening and counterscreening procedures to identify cell-type specific cis regulatory elements. The vector, if it is of viral origin may not require propagation in a bacterial host. However, more typically the vector requires propagation in, e.g., *E. coli*, and contains sequences necessary for replication and selection in *E. coli* such as a colE1 replicon and an antibiotic resistance gene.

Reporter Genes

Numerous reporter genes have been appropriated for use in expression monitoring and in promoter/enhancer trapping. A reporter comprises any gene product for which screens or selections can be applied. Reporter genes used in the art include the LacZ gene from *E. coli* (Shapiro S. K., Chou J., et al., *Gene* November 25: 71–82 (1983)), the CAT gene from *E. coli* (Thiel G., Petersohn D., and Schoch S., *Gene* February 12; 168: 173–176 (1996)), the luciferase gene from firefly (Gould S. J., and Subramani S., *Anal Biochem* November 15; 175: 5–13 (1988)), and the GFP gene from jellyfish (Chalfie M. and Prashner D. C., U.S. Pat. No. 5,491,084). This set has been primarily used to monitor expression of genes in the cytoplasm. A different family of genes has been used to monitor expression at the cell surface, e.g., the gene for lymphocyte antigen CD20. Normally a labeled antibody is used that binds to the cell surface marker (e.g., CD20) to quantify the level of reporter (Koh J., Enders G. H., et al. *Nature* 375: 506–510 (1995)).

Of these reporters, GFP and the cell surface reporters are potentially of greatest use in monitoring living cells, because they act as "vital dyes." Their expression can be evaluated in living cells, and the cells can be recovered intact for subsequent analysis. It is also very useful to employ reporters whose expression can be quantified rapidly and with high sensitivity. Thus, fluorescent reporters (or reporters that can be labeled directly or indirectly with a fluorophore) are especially preferred. This trait permits high throughput screening on a machine such as a FACS.

GFP is a member of a family of naturally occurring fluorescent proteins, whose fluorescence is primarily in the green region of the spectrum. GFP has been developed extensively for use as a reporter and several mutant forms of the protein have been characterized that have altered spectral properties (Cormack B. P.; Valdivia R. H., and Falkow S., *Gene* 173: 33–38 (1996)). Wild type GFP absorbs maximally at 395 nm and emits at 509 nm. High levels of GFP expression have been obtained in cells ranging from yeast to human cells. It is a robust, all-purpose reporter, whose expression in the cytoplasm can be measured quantitatively using instruments such as the FACS.

Libraries

Genetic libraries typically involve a collection of DNA fragments, usually genomic DNA or cDNA, but sometimes synthetic DNA or RNA, that together represent all or some portion of a genome, a population of mRNAs, or some other set of nucleic acids that contain sequences of interest. Typically, genetic libraries represent sequences in a form that can be manipulated. A total genomic DNA library in principle includes all the sequences present in the genome of an organism propagated as a collection of cloned sequences. It is often desirable to generate a library that is as representative of the input population of nucleic acids as possible. For example, sequences that are present at one to one ratios in the input population (e.g., gnome) are present in the library in the same proportion. To achieve reasonable (e.g, >99% predicted) representation of the nucleic acid sequences that the library is intended to contain, it is essential to have more than 5-fold coverage; that is, the library must contain a 5-fold excess of total inserts beyond the total number required theoretically to cover the collection of nucleic acid sequences one time. For example, if the library is intended to represent the genome of an organism, coverage =the total number of inserts multiplied by the mean insert size divided by the genome size. Typically libraries are propagated in vectors that grow in bacterial cells, although eukaryotic cells such as yeast and even human cells can also serve as hosts.

The mean insert size of a library is a variable that can be manipulated within rather broad limits that depend on vector and cell types, among other things. For example, some vectors such as bacterial plasmids accommodate small inserts ranging from a few nucleotides to a few kilobasepairs, whereas others such as yeast artificial chromosomes can accommodate insert sizes that exceed 1,000 kilobasepairs. Certain applications in molecular biology are best suited to large inserts (e.g., mapping the human genome), whereas other applications favor smaller fragments.

Library construction conditions can also be varied to bias the final library such that it contains primarily single inserts (monomers) or multiple inserts. Multiple inserts allow sampling of different combinations of sequences that might not be sampled if single inserts are chosen. For instance, enhancer/promoter combinations that either do not exist in vivo, or that lie so far apart on the chromosome that they cannot physically be contained in a single-insert-containing expression vector. Smaller fragments and higher insert:vector ligation ratios favor multiple inserts. In addition, if the cloning involves insertion into a vector that has been linearized with two different sticky ended sites, it is possible to apply a strong bias toward, e.g., double inserts. The probability that a recombinant clone is derived from a three-part ligation (vector plus two inserts) is enhanced by forcing the rejoining to occur through a sticky end common to two insert fragments that is different from the two sticky ends of the vector.

The invention described herein most preferably uses genetic libraries that contain inserts on the smaller end of the spectrum. These inserts would most typically be derived from genomes of particular organisms, and would range from, e.g., 10 base pairs to 10 kilobase pairs. The libraries most typically would initially be constructed from total genomic DNA and would be as representative as possible. The details of library construction, manipulation, and maintenance are known in the art (Ausubel F., Brent R. et al., 1996; Sambrook J., Fritsch E. F., and Maniatis, T., 1989). In one embodiment of the invention a library is created according to the following procedure using methods that are well-known in the art. Total genomic DNA is isolated and fragmented to an average size of between 500 and 5,000 base pairs by sonication or by enzymatic digestion. If sonication is used, these fragments are treated with enzymes to repair their ends. The fragments are ligated into a dead expression vector of the type described infra. The ligated material is introduced into E. coli and clones are selected. A number of individual clones sufficient to achieve 5-fold coverage is collected, and grown in mass culture for isolation of the resident vectors and their inserts. This process allows large quantities of the library DNA to be obtained in preparation for subsequent experiments described below. Other ways to make genetic libraries include those described in Ausubel F., Brent R. et al., 1996.

In specific embodiments of the invention, it is preferable to use non-natural nucleic acid as the starting material for the library. For example, it may be desirable to use a population of synthetic oligonucleotides, e.g., representing all possible sequences of length N, as the input nucleic acid for the library. In addition, it may be desirable to use mixtures of natural and non-natural nucleic acids for library inserts.

Nucleic Acid Transfer

During the last two decades several basic methods have evolved for transferring exogenous nucleic acid into host cells. These methods are well-known in the art (Ausubel F., Brent R. et al., 1996; Sambrook J., Fritsch E. F., and Maniatis T., 1989). Some methods give rise primarily to transient expression in host cells; i.e., the expression is gradually lost from the cell population. Other methods can also generate cells that stably express the transferred nucleic acid, though the percentage of stable expressers is typically lower than transient expressers. Such methods include viral and non-viral mechanisms for nucleic acid transfer.

In the case of viral transfer, a viral vector is used to carry nucleic acid inserts into the host cell. Depending on the specific virus type, the introduced nucleic acid may remain as an extrachromosomal element (e.g., adenoviruses, Amalfitano A., Begy C. R., and Chamberlain J. S., *Proc. Natl. Acad. Sci. USA* 93: 3352–3356 (1996)) or may be incorporated into a host chromosome (e.g., retroviruses, Iida A., Chen S. T. et al., *J. Virol* 70: 6054–6059(1996)).

In the case of non-viral nucleic acid transfer, many methods are available (Ausubel F., Brent R. et al., 1996). One technique for nucleic acid transfer is $CaPO_4$ coprecipitation of nucleic acid. This method relies on the ability of nucleic acid to coprecipitate with calcium and phosphate ions into a relatively insoluble $CaPO_4$ grit, which settles onto the surface of adherent cells on the culture dish bottom. The precipitate is, for reasons that are not clearly understood, absorbed by some cells and the coprecipitated nucleic acid is liberated inside the cell and expressed. A second class of methods employs lipophilic cations that are able to bind DNA by charge interactions while forming lipid micelles. These micelles can fuse with cell membranes, dumping their DNA cargo into the host cell where it is expressed. A third method of nucleic acid transfer is electroporation, a technique that involves discharge of voltage from the plates of a capacitor through a buffer containing DNA and host cells. This process disturbs the bilayer sufficiently that DNA contained in the bathing solution is able to penetrate the cell membrane.

Several of these methods often result in the transfer of multiple DNA fragments into individual cells. It is often difficult to limit the quantity of DNA taken up by a single cell to one fragment. However, methods are known in the art to minimize transfer of multiple fragments. For example, by using "carrier" nucleic acid (e.g., DNA such as herring sperm DNA that contains no sequences relevant to the experiment), or reducing the total amount of DNA applied to the host cells, the problem of multiple fragment entry can be reduced. In addition, the invention does not specifically require that each recipient cell have a single type of library sequence. Multiple passages of the library through the host cells (see below), permit sequences of interest to be separated ultimately from sequences that may be present initially as bystanders. Moreover, the presence of multiple independent vector/insert constructs in a cell may be an advantage in certain cases because it allows more library inserts to be screened in a single experiment.

Although both transient and stable expression can be employed in the invention, transient expression may be preferable in many cases. First, more cells generally express sequences transiently than stably, so more library inserts can be assayed in a single experiment. Second, the experiments can be done more rapidly using transient expression.

A potential pitfall of transient expression involving mammalian cells is that most cells express multiple copies of the transferred library sequences; i.e., several independent inserts (and their linked expression vectors) are present in nearly every cell that accepts the exogenous DNA. This can confound the analysis in some cases. However, in the experiment described herein, this property of transient expression is actually advantageous because it allows more library sequences to be tested. Thus, if one million cells accept transferred library sequences and, on average, each host cell expresses ten transferred sequences, a total of ten million inserts can be assayed for their effect on gene expression. Since the large majority of sequences are not expected to activate expression, the few cells that do express GFP can be separated by FACS, and their library inserts can be recovered. Among the sequences that activate expression will be a ten-fold excess of those that were present as bystanders in the recovered cells. These bystanders can be removed in subsequent cycles of enrichment. In summary, the property of transient expression that leads to multiple expressers per cell can be used to advantage in the present invention to allow screening of a larger number of library sequences in the first screening step. In the counterscreening step, it is advantageous to minimize the number of inserts per cell, because cis sequences that confer low expression will be obscured or dominated by those in the same cell that confer high expression.

Many procedures have been adapted to introduce DNA in solution into host cells. One of the most general involves electroporation. Conditions vary from cell type to cell type. Typically experiments must be carried out initially to determine the parameters that maximize expression of exogenous nucleic acid. For example, a set of electroporation protocols are performed in which a particular cell type is exposed to, e.g., a GFP expression vector (such as pEGFP-C1), each protocol using a specified voltage and capacitance. The experiment that yields the largest number of bright cells after one or two days of incubation reveals the optimum conditions for electroporation of that cell type.

Positive and Negative Enrichment and Passaging

The combination of genetic libraries and genetic selection or screening techniques permits identification of specific sequences from libraries based on their functions in living cells. This strategy has been used frequently in molecular biology to clone genes based on expression, e.g., by complementation of a mutant phenotype. The premise of the strategy is that an appropriately constructed library can be introduced into suitable host cells and the effects of the library sequences can be monitored. For example, a particular host may die in the absence of the wild type function of a gene; the host cell will only grow when a library insert that includes the gene is present. Alternatively, screens can be employed to pick out the library sequences that confer a particular phenotype.

In a preferred embodiment of the present invention, cis regulatory sequence functions of specific library sequences are monitored in living host cells via expression of a reporter such as GFP. To identify cis regulatory sequences, the genetic libraries are constructed in dead or low activity expression vectors that, in the absence of library inserts, do not express appreciable levels of reporter, such as the vector illustrated in FIG. 1(B). However, if a particular cis regulatory sequence is introduced, e.g., upstream of the reporter, reporter expression ensues. Such expression can be observed by passage of host cells through a flow cytometer or equivalent device (Robinson J. P., Darzynkiewicz Z. et al. (Eds.), *Current Protocols in Flow Cytometry*, John Wiley and Sons, New York (1997)). In addition, individual cells that express reporter protein can be recovered and separated from cells that do not by a FACS.

If a library carried in a dead or low activity GFP expression vector such as that described above is introduced into a population of host cells, e.g., cultured mammalian cells, a large fraction of the cells that obtain library clones are likely to be negative or weakly positive for GFP expression. These cells contain vectors with insert fragments that do not activate transcription. In addition, depending on how the library is introduced into cells, a significant fraction of the host cells may be negative because they do not take up any library DNA whatsoever. A few cells, however, may be bright because they harbor expression vectors with inserts that activate GFP expression.

Figure 2A:
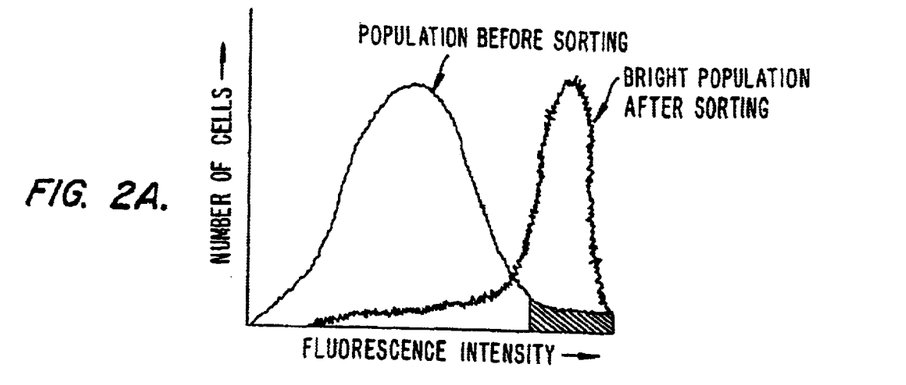

If this population of host cells, some or all of which harbor expression vectors from the library, is passed through a FACS, a profile of fluorescence can be obtained (FIG. 2(A)). This profile will include on the left end cells that are negative for GFP ("dim" cells), in the middle cells that express intermediate amounts of GFP, and on the right tail of the distribution cells that express large amounts of GFP. Such positive bright cells can be selected from the population using the FACS, and their library insert sequences can be isolated, e.g., by PCR. If the library insert sequences are isolated without the expression vector sequences, the isolated sequences are inserted back into the expression vector before proceeding to the next step. Alternatively, methods that isolate the entire recombinant construct (i.e. library inserts along with vector sequences) may be employed using known techniques (Ausubel F., Brent R. et al., 1996; Sambrook J., Fritsch E. F., and Maniatis T., 1989). These sequences represent a sub-library of sequences capable of activating GFP expression in the host cells. In addition, depending on the details of the nucleic acid transfer procedure, a number of other sequences that do not activate GFP expression may also be present. Nevertheless, this procedure allows enrichment from the original library for selected sequences that activate reporter expression in the host cells. To further enrich the sub-library, multiple cycles of nucleic acid transfer of this sub-library into the first host cells followed by FACS analysis can be carried out.

Figure 2B:
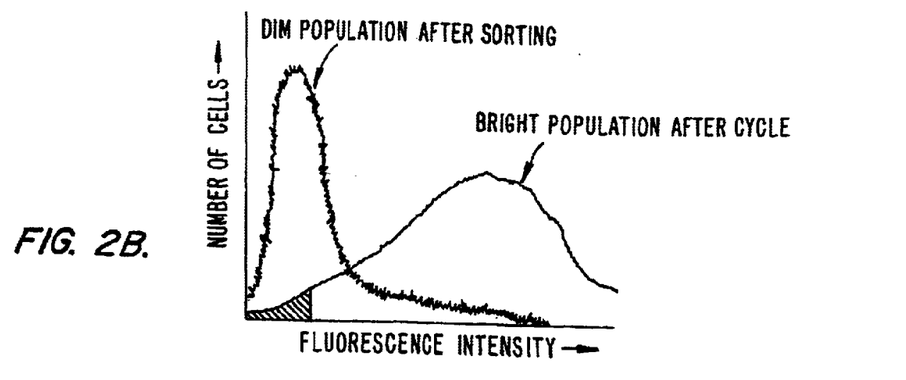
Figure 2C:
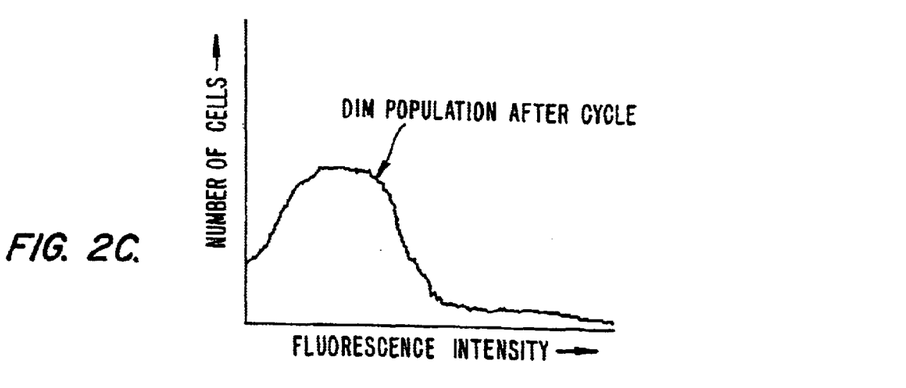
Figure 3:
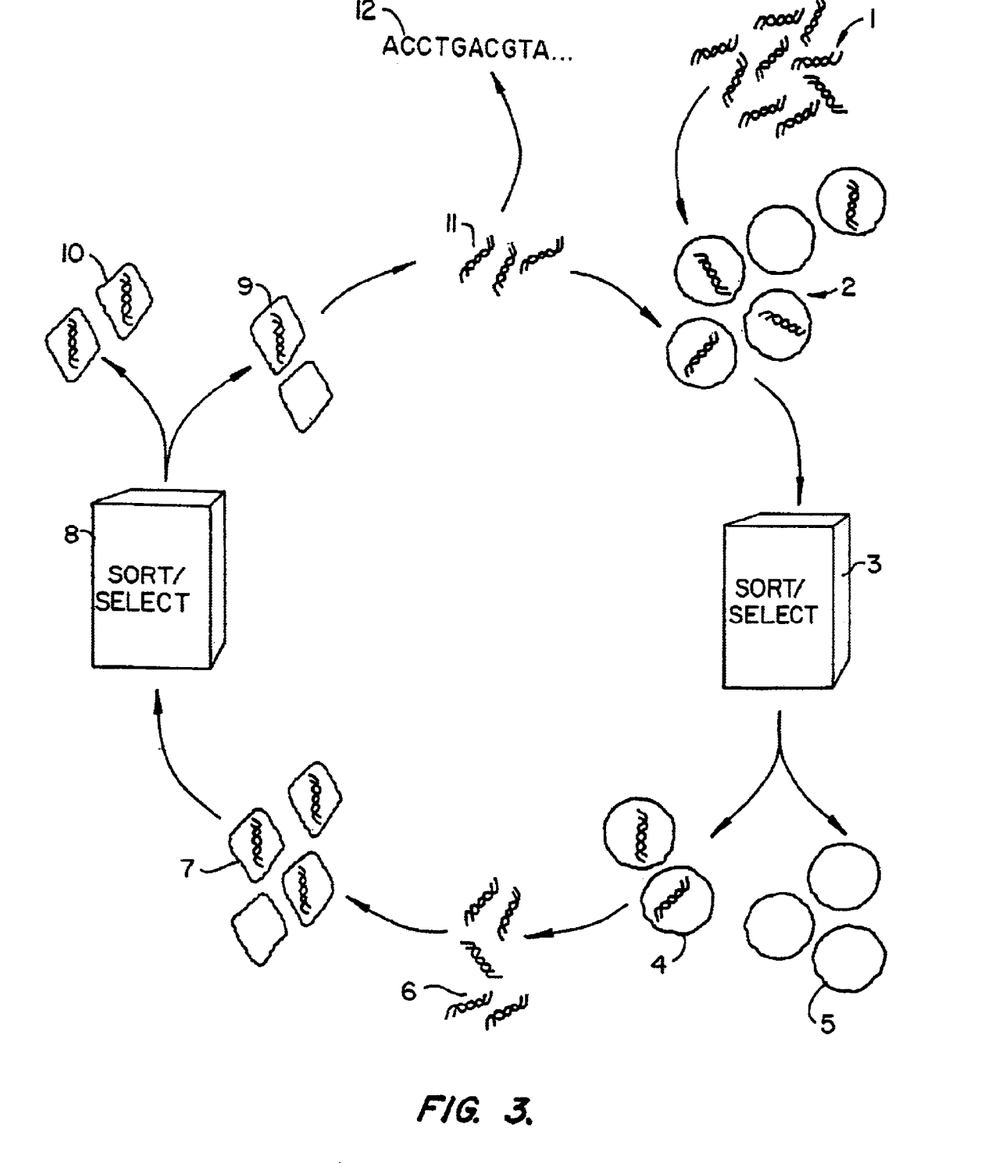

The sub-library isolated as above can now be counterselected in a second host cell to enrich for sequences that are active in promoting expression of the reporter in the first host cell, but not in the second host cell, as illustrated in FIG. 2(B). The positively selected sub-library is introduced into the second host cell, allowed to express GFP, and then analyzed by FACS. Instead of collecting bright cells that fall on the right side of the distribution, dim cells on the left side are recovered. These contain (perhaps among other things) cells harboring sub-library sequences that are active in the first host cell, but do not promote gene expression in the second host cell. Such sequences therefore are selectively active. As with the positive selection, the the sub-library isolated from the second host cells can be further enriched by multiple cycles of nucleic acid transfer of this sub-library into the second host cells followed by FACS analysis. The process of positive and negative enrichment can be continued for several rounds to ensure that the sub-library sequences ultimately identified are indeed selectively active. FIG. 2(C) illustrates the fluorescence intensity profile obtained by introducing the sub-library isolated from the second host cells back into the first host cells. FIG. 3 illustrates the above-described selection/counterselection scheme.

The invention also can be used to identify cell-type specific negative regulatory sequences. These are cis regulatory sequences that down-regulate the expression of nearby sequences in specific cell types. Conceptually, this is a mirror image approach of that used for identifying promoter or enhancer sequences. The parent vector used is capable of moderate to high reporter expression in the host cells used in the method. A library of fragments is cloned using this "live" vector and is introduced into a first host cell (e.g. non-tumor cells). The cells are screened for reporter expression, and those cells that do not express appreciable levels of reporter ("dim" cells) are selected as candidates that contain negative regulatory sequence inserts. A counter screening step is carried out by isolating a sub-library from the selected first host cells, introducing the sub-library into the second host cell (e.g. tumor cells), and collecting cells on the right side of the distribution ("bright" cells). These contain (perhaps among other things) cells harboring sub-library sequences that repress gene expression in the first cell type, but do not repress gene expression in the second cell type. The process of negative and positive enrichment can be continued for several rounds to ensure that the sub-library sequences ultimately identified are selective.

It is also possible to use other methods of enrichment besides FACS analysis to detect and identify cis sequences that have desirable properties. The present invention can be used in the context of, e.g., antibody panning for positive and negative enrichment (Simmons D., and Seed B., *J Immunol* 141:2797–2800(1988)). In addition, there are methods known in the art whereby individual cells can be scanned on a microscope slide or similar surface and collected serially by the action of a robot (Quixell Cell Selection and Transfer System; Stoelting Co., Wood Dale, Ill.). These alternatives lack some of the advantages of FACS analysis, especially speed (automated collection by robot from slides) and quantitation (antibody panning).

Evolution of Novel Regulatory Elements

The invention permits identification of novel regulatory elements that involve sequence variants, combinations and permutations of natural promoters, enhancers, negative regulatory sequence elements, and/or synthetic DNA sequences. The methods used to create such non-natural sequences include the following types of manipulations. Sub-library sequences that have a particular activity are either mutated in vitro by any of several methods known in the art, or rejoined with other natural or non-natural fragments by ligation, or digestion and re-ligation (Ausubel F.

M., Brent R., et al., 1996). These new sub-libraries are passaged through the same host cells (or different cell types) and the selection and counter selection steps are repeated. The method thus permits the evolution of more desirable properties in a series of steps that involve manipulation of library sequences in vitro followed by selection in vivo. Thus, it is possible to evolve, e.g., a cis sequence that is more completely "off" in one cell type and more active in another.

Mechanisms

The present invention provides the basis for rapidly elucidating the mechanism by which specific cis sequences confer cell-type-selective expression or repression. Once such cell-specific cis sequences are identified, it may be possible to predict which protein factors are responsible for the selectivity based on the cis sequences alone. For example, public domain databases such as TRANSFAC contain DNA sequences that have been determined to bind specific transcription regulatory factors. A search of these types of databases may reveal the identities of the relevant transcription factors that activate (or repress) transcription of the reporter gene in particular host cells.

Alternatively, it is possible to use biochemical methods to identify the molecules whose binding is responsible for the cell-specific behavior of the sequences. There are many techniques known in the art suitable for carrying out such biochemical studies (Latchman D. S., 1996; McKnight S. L. and Yamamoto K. R., 1992). For example, the cis sequences can be used as affinity reagents to bind transcription factors from protein extracts prepared from cells. Gel mobility shift assays are a simple means for demonstrating a difference between binding factors from the two (or more) host cells used to select the cis sequences. Such bound factors can be purified biochemically using the gel shift experiments as an assay. It may also be possible to use mass spectrometry to analyze bound factors directly. The cis sequence is used to bind protein factors from cell extracts. After washing, the bound proteins are eluted from the DNA, proteolytically cleaved, and subjected to mass analysis on a mass spectrometer (Shevchenko A., Jensen O. N., et al., *Proc. Natl. Acad. Sci USA* December 10; 93: 14440–14445 (1996)) From the mass of the protein fragments, it is sometimes possible to determine from a public protein database (such as GenPept) the identity of proteins that give rise to such proteolytic digestion products.

Cis Sequences that Affect Translation or mRNA Stability

The present invention also can be adapted so that cis sequences that affect protein translation and/or mRNA stability can be identified. To identify such sequences, a variation of the procedures described above is used. The library of DNA fragments is inserted downstream from a functional promoter in such a position that each insert fragment lies adjacent to the reporter gene coding sequence on the transcript generated from the expression construct. Sequences that enhance or diminish expression can be identified by an appropriate series of screening and counterscreening experiments. Subsequently, effects on transcription can be sorted out from effects on translation/stability.

Identification of Molecules Capable of Interacting with Cell-Specific Cis Sequences Another use of cis sequences identified as described herein involves further genetic experiments to identify proteins that influence expression of the reporter in a cell-type-dependent manner. These experiments incorporate cis sequences linked to the reporter (e.g., GFP) in a condition such that the expression construct is stable. Thus, the expression construct (including the selected cis sequence) is placed in particular host cells (e.g., mammalian cells in culture) so that the vector is stably propagated. The expression construct may be maintained on a vector that propagates extrachromosomally, or it may be inserted into the host cell chromosomal DNA. In either case, such host cells can be used as the recipient for subsequent screening by FACS to identify variant cells that no longer express the reporter (or variant cells that do express the reporter from an initial population that do not). These variant cells can be used in principle to define other genetic components that influence expression of the reporter. For example, if a genetic expression library is introduced into the host cells, variants can be identified that have altered reporter expression properties. These can be selected on the FACS, and their resident library inserts can be isolated and characterized.

EXAMPLE 1

Identification of Cis Sequences Associated with the Galactose-Regulated Transcriptional Network of *S. cerevisiae*

The galactose-regulated transcriptional network is comprised of at least five genes in yeast that are rapidly induced to high levels in the presence of galactose and repressed in the presence of glucose (Johnston M., *Microbiol. Rev.* 51, 4: 458–476 (1987)). The method of the invention is applied to yeast grown in the presence of these two alternative carbon sources to identify enhancer regions of the GAL 1,2,7, 10 and MEL 1 genes, and perhaps others.

Construction of a Promotorless GFP Vector for *S. cerevisiae*

Figure 4:
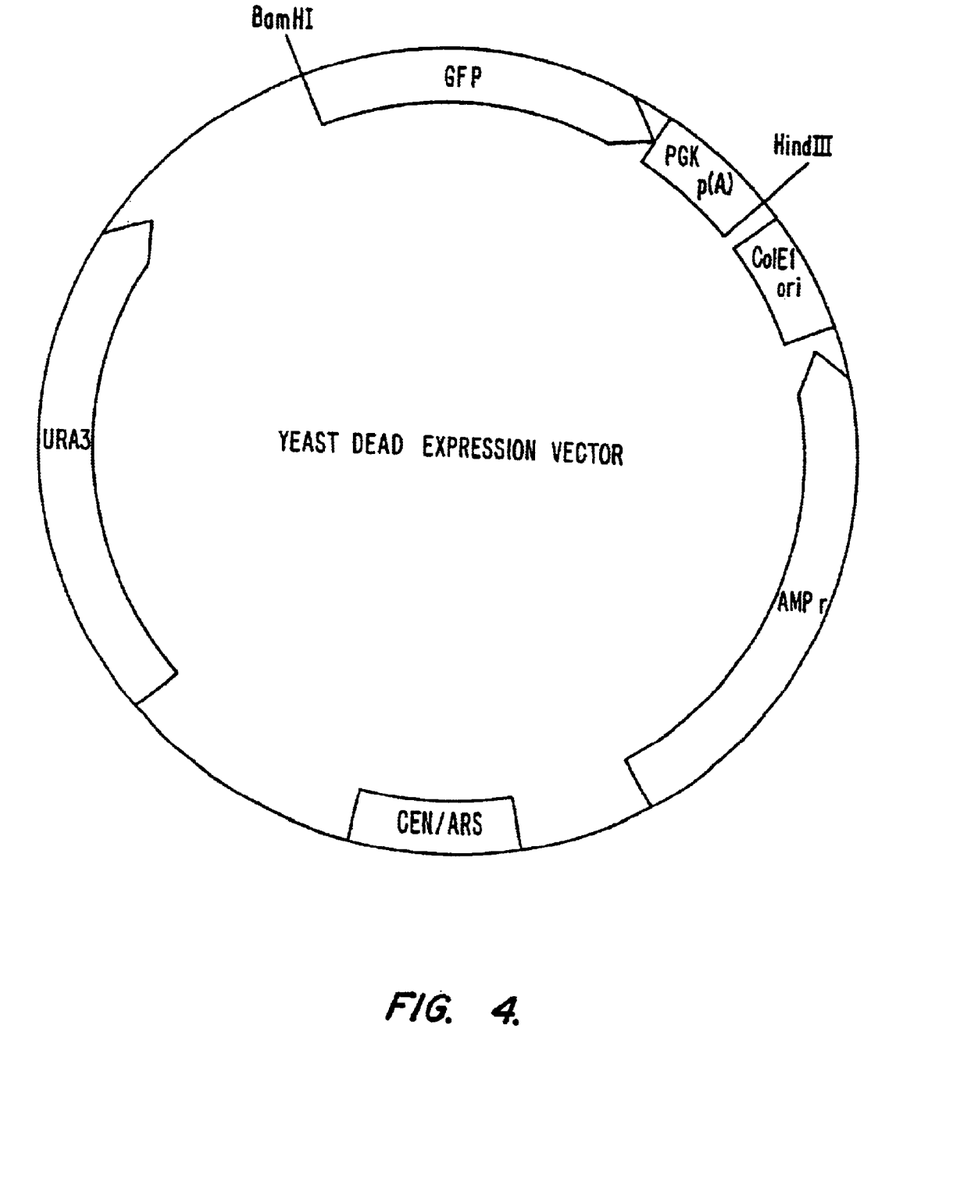
FIG. 4: Dead yeast expression vector diagram.

A GFP variant previously established to be highly fluorescent in yeast is amplified by PCR to generate a DNA fragment containing the GAL1TATA box and mRNA start site placed 5' (upstream) of the GFP coding region, which in turn is located 5' of the yeast PGK1 3' untranslated region (UTR). The 5' and 3' end of this PCR product contain BamH1 and HindIII restriction enzyme sites, respectively, in order to facilitate cloning into the shuttle vector pRS416 (Sikorski R. S., and Hieter P., *Genetics* 122:19–27 (1989)). This operation creates the vector pRS416-GFP which contains the URA3 and β-lactamase (Amp) genes for selection in yeast and bacteria, respectively (FIG. 4). In addition pRS416-GFP contains CEN and ARS sequences for efficient replication and segregation in yeast. When introduced into yeast, pRS416-GFP produces no appreciable fluorescence in the presence of galactose or glucose.

Insertion of a Yeast Genomic Library

Yeast genomic DNA is isolated and sheared by sonication. Overhanging and recessed 5' and 3' ends are made blunt with T4 DNA polymerase and BamH1 linkers are ligated to the blunt ends. DNA fragments of 250–1400 nucleotides are collected after electrophoresis through 1% agarose. These fragments are ligated into BamH1-digested pRS416-GFP and introduced into *E. coli*. Selection for Amp-positive clones allows recovery of independent clones for analysis.

Identification of Yeast Cells that Express GFP

The library is introduced into yeast by standard techniques (Ausubel F. M., Brent R., et al., 1996). Approximately 10×10⁶ primary transformants are collected, pooled and stored. An aliquot of these transformants is grown in liquid media containing galactose and raffinose as a carbon source for sufficient time (4–12 hours) to allow expression of GFP. Yeast cells are sorted into the bright and dim fractions according to the amount of baseline fluorescence observed for the dead expression vector. The bright population of yeast cells is collected and grown in liquid media containing dextrose [glucose] as a carbon source for sufficient time to allow GFP to clear from the cell. An aliquot of these yeast are again sorted into bright and dim fractions and the dim fraction is plated to recover single colonies on selective (i.e. ampicillin-containing) media.

Yeast arising from single colonies are reanalyzed by FACS after growth under inducing or repressing conditions to confirm the behavior of the clones selected under the regime described above. Plasmids are isolated from the yeast and the 5' and 3' ends of the genomic DNA inserts are sequenced. Among the sequences recovered are those encoding the enhancer regions of the GAL 1,2,7, 10 or MEL 1 genes.

EXAMPLE 2

Identification of Cis Regulatory Elements Active Specifically in Metastatic Melanoma Cells This example of the invention uses two related cell types: a metastatic melanoma cell line (e.g., HS294T) and an early melanoma cell line or a cell line established from normal tissue (e.g., melanocytes) (Satyamoorthy K., DeJesus E., et al., *Melanoma Research* (1997) [in press]) The method is used to identify cis regulatory sequences that confer expression of the GFP reporter in the metastatic cells and not in the second cell line. Such sequences may be used to drive expression of a reporter gene that, upon introduction into tissue biopsies for example, reveals the presence of metastatic tumor tissue. The cis sequences may also be useful in the context of gene therapy, for example in directing expression of an exogenous toxin gene selectively in the metastatic cells.

Construction of a Promoterless Mammalian Expression Vector pEGFP-C1 (Clontech Laboratories, Palo Alto, Calif.; GenBank accession number U55763) is used as a starting material to construct the parental vector. It contains the GFP coding sequence flanked by a CMV promoter/enhancer on its 5' side, and the SV40 T-Antigen gene polyadenylation signal on the 3' side (FIG. 1). This vector is modified so that upstream of the GFP translational start codon are sequences that either include part of the functional promoter (the TATA box from the CMV promoter, generated by trimming pEGP-C1 to a position −63 base pairs from the translational start codon), or sequences completely missing the promoter (trimmed to −10 base pairs upstream of the GFP start). These two crippled ("dead") expression vectors lack sequences necessary for GFP expression in most mammalian cells. The vector is further engineered so that restriction enzyme recognition sites, useful for inserting library fragments, are introduced at positions −63 and −69.

Preparation of Genetic Libraries

Genetic libraries are constructed in dead expression vectors such as those described in the preceding section are constructed from DNA derived from various sources.

One source is oligonucleotide synthesis; e.g., synthetic DNA produced on an automated DNA synthesizer. This DNA may represent all sequences of a certain length (e.g., a collection of all one million possible sequences of length 10), or may represent a subset of such sequences (e.g., one million of the possible one trillion 20-mers). These sequences are prepared in such a way that they are compatible for insertion into the expression vectors; for instance, they have adapters at their ends that are appropriate for amplification followed by restriction enzyme digestion to generate sticky ends that facilitate ligation of library inserts into the expression vector.

A second source of library DNA for insertion involves genomic DNA that has been sheared mechanically or fragmented with an enzyme and separated by size. Typically, the ends of such fragmented DNA are ragged; that is, they contain a high proportion of 3' and 5' overhangs that must be eliminated or repaired prior to cloning. Numerous methods for such repair are known in the art including enzymatic repair with a polymerase such as T4, T7, or Pfu DNA polymerase, or treatment with Mung Bean nuclease (Ausubel F., Brent R. et al., 1996; Sambrook J., Fritsch E. F., and Maniatis T., 1989). These treatments render a higher proportion of the fragment ends flush, suitable for direct blunt-end cloning, or preferably, attachment of adapters that can be used to insert the fragments into the expression vector. In this example, it is preferable to introduce BamH1 adapters by ligation, to gel purify the ligated fragments, and to ligate these fragments using their attached adapters into the cloning site of the parent vector.

In certain cases it is helpful to limit the size of the insert DNA of the genetic library. Depending on the time and intensity of the shearing protocol, different mean sizes of the fragments will result. The fragments of appropriate size can be separated from other fragments by, e.g., gel electrophoresis and excision of the relevant gel region using standard methods that are known in the art (Ausubel F., Brent R. et al., 1996; Sambrook J., Fritsch E. F., and Maniatis T., 1989). To further control the size of the input fragments, enzymatic digestion of genomic DNA is also possible. For instance, the double-strand-specific, processive exonuclease Bal-31 can be used to generate a reasonably homogeneous set of fragments of a particular size range by titrating the reaction conditions. This digested set of fragments can be further selected on gels.

Nucleic Acid Transfer

The genetic expression library must be introduced into host cells to allow expression of the reporter. This can be accomplished in numerous ways.

For the purposes of the experiment described here, transient expression is optimal, because it is most rapid and efficient. For the same reasons, electroporation is a good choice as a means for introducing the genetic library.

After electroporation conditions are determined, a large number of cells (e.g. twenty million) are collected for electroporation. One of the genetic library types described in this example is introduced into the metastatic melanoma cells and the cells are left in culture long enough to allow expression of the reporter (typically one to two days). This procedure generally results in 1–50% of the cells expressing transferred DNA. As a control experiment, GFP under the regulation of the CMV promoter is introduced into the same cells. The expression profile of these cells is used to set the photomultiplier tube baseline (voltage gain) for the subsequent analysis. The library-containing cells are harvested and passed through the FACS. Cells that express GFP (greater than, e.g., two standard deviations above the mean level of fluorescence of the population) are collected and used to isolate their inserts by PCR.

The set of library inserts selected in the first FACS experiment may be reintroduced into the expression vector using the same basic procedure described above to enrich further prior to the counterscreening step. The ligated material is transformed into E. coli, amplified by growth, and reisolated. This DNA sub-library is introduced into the host cells for another round of selection. Following isolation of the inserts and recloning in the expression vector, the sub-library is ready for the counterscreening procedure.

The sub-library is introduced into the second host cell type (e.g., early melanoma or normal melanocyte) using a procedure that minimizes the probability of multiple expressed inserts per cell, and grown for one to two days to allow GFP expression. These cells are examined with the FACS, but this time dim cells on the left side of the fluorescence intensity distribution are collected. Among these cells are those that did not receive expression constructs and those that contain inserts that are active in metastatic melanoma cells, but inactive in the second cell type. These inserts can be recovered by PCR and the entire process of selection-counterselection can be repeated as many times as necessary. The final collection of cis regulatory fragments can be cloned in E. coli, and individual clones selected for further study, including DNA sequence analysis. Cis sequences identified in this manner have the valuable property of stimulating transcription selectively in metastatic melanoma cells. The extent and the mechanism of such selectivity can be defined in subsequent experiments.

EXAMPLE 3

Identification of Cis Regulatory Sequences Specific to p16-Arrested Melanoma Cells In certain situations, it is useful to identify cis sequences that promote transcription in arrested cells as compared to growing cells or vice versa. These sequences may be useful as markers of the arrested (or non-arrested) state, or as adjuncts to gene therapy. To illustrate how such sequences may be identified, p16-arrested HS294T metastatic melanoma cells are used in association with non-arrested HS294T cells. An expression-construct containing the human p16 gene under control of an IPTG-regulated promotor is introduced stably into HS294T cells. When IPTG is added to the medium, these cells ectopically express p16 and arrest in the G1 phase of the cell cycle. (Stone S., Dayananth P., and Kamb A., Cancer Research 56; 3199–3202(1996)).

In contrast, the parental HS294T cells do not arrest and continue to divide asynchronously. The two cell types, HS294T and HS294T/p16 provide the basis for identification of cis regulatory elements that are active in p16-arrested HS294T cells and not in growing HS294T cells.

One of the expression libraries described in Example 2 is introduced into HS294T/p16 cells by electroporation and the cells are exposed to IPTG. This procedure generally results in about 10–50% of the cells expressing transferred DNA. As a control experiment, GFP under the regulation of the CMV promoter is introduced into the same cells. The expression profile of these cells is used to set the photomultiplier tube baseline (voltage gain) for the subsequent analysis. Twenty million HS294T/p16 cells are collected and used for electroporation. These cells are plated in the presence of IPTG and, after two days, the arrested cells are harvested and passed through the FACS. Cells that express GFP (greater than, e.g., two standard deviations above the mean level of fluorescence) are collected and used to isolate their inserts by PCR.

The set of library inserts selected in the first FACS experiment is reintroduced into the expression vector using the same basic procedure described above. The ligated material is transformed into E. coli, amplified by growth, and reisolated. This DNA sub-library may be introduced into the HS294T/p16 host cells for another round of selection, if necessary. Following isolation of the inserts and recloning in the expression vector, the sub-library is ready for the counterscreening procedure.

The sub-library is introduced into HS294T/p16 cells and grown in the absence of IPTG for two days. These cells are examined with the FACS, but this time, cells on the left side of the fluorescence intensity distribution are collected. Among these cells are those that did not receive expression constructs and those that contain inserts that are active in p16-arrested HST294T cells, but inactive in growing HS294T cells. These inserts can be recovered by PCR and the entire process of selection-counterselection can be repeated as many times as necessary. The final collection of cis regulatory fragments can be cloned in E. coli, and individual clones selected for further study, including DNA sequence analysis.

The present invention is not to be limited in scope by the exemplified embodiments which are intended as illustrations of single aspects of the invention, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited within the body of the instant specification are hereby incorporated by reference in their entirety.

What is claimed is:

1. A method for identifying cell-type specific cis-regulatory elements, comprising the steps of:
   (a) generating a library of synthetic oligonucleotides in an expression vector comprising a sequence encoding a reporter molecule;
   (b) introducing the library into a first population of host cells;
   (c) selecting from said first population of host cells a first subpopulation of host cells having a first predetermined level of reporter gene expression;
   (d) recovering from said first subpopulation of host cells a pooled sub-library of synthetic oligonucleotides;
   (e) introducing said pooled sub-library into a second host cell population;
   (f) counterscreening said second host cell population to identify members of said second host cell population having a second predetermined level of reporter gene expression which is distinct from said first predetermined level; and
   (g) recovering cell-type specific cis-regulatory elements from said members having said distinct second predetermined level of reporter gene expression.

2. A method for identifying cell-type specific cis-regulatory elements, comprising the steps of:
   (a) generating a library of oligonucleotides derived from naturally-occurring nucleotide sequences in an expression vector comprising a sequence encoding a reporter molecule;
   (b) introducing the library into a first population of host cells;

(c) selecting from said first population of host cells a first subpopulation of host cells having a first predetermined level of reporter gene expression;

(d) recovering from said first subpopulation of host cells a pooled sub-library of oligonucleotides;

(e) introducing said pooled sub-library into a second host cell population;

(f) counterscreening said second host cell population to identify members of said second host cell population having a second predetermined level of reporter gene expression which is distinct from said first predetermined level; and (g) recovering cell-type specific cis-regulatory elements from said members having said distinct second predetermined level of reporter gene expression.

3. The method of claim 1 or 2, further comprising reintroducing the cell-type specific cis-regulatory elements recovered in step (g) into the first population of host cells, and repeating steps (c) through (g).

4. The method of claim 3, wherein the cell-type specific cis-regulatory elements recovered in step (g) are manipulated in vitro prior to the reintroducing step.

5. The method of claim 4, wherein the manipulation in vitro is alteration of the cell-type specific cis-regulatory elements by a technique selected from the group consisting of mutation in vitro and recombination in vitro.

6. The method of claim 1 or 2, further comprising reintroducing the pooled sub-library of oligonuclootides recovered in step (d) into the first population of host cells, and repeating step (c).

7. The method of claim 1 or 2, further comprising reintroducing the cell type specific cis-regulatory elements recovered in step (g) into the second population of host cells, and repeating step (f).

8. The method of claim 1 or 2, wherein the pooled sub-library of oligonucleotides recovered in step (d) and the cell-type specific cis-regulatory elements recovered in step (g) include expression vector sequences.

9. The method of claim 1 or 2, wherein the expression vector further comprises a second sequence encoding a second reporter molecule.

10. The method of claim 1 or 2, wherein the steps of selecting comprise the use of a fluorescence activated cell sorter.

11. The method of claim 1, wherein said library of synthetic oligonucleotides comprises all possible sequences of a pre-selected length of up to about 10.

12. The method of claim 1, wherein said library of synthetic oligonucleotides comprises a subset of all possible sequences of a pre-selected length.

* * * * *